ized States Patent (12) United States Patent
Lohitharn (10) Patent No.: US 10,144,943 B2
(45) Date of Patent: Dec. 4, 2018

(54) SEMI-CONTINUOUS PROCESS FOR THE PRODUCTION OF RHAMNOLIPIDS AT HIGH YIELD AND TITER

(71) Applicant: Logos Technologies, LLC, Chantilly, VA (US)

(72) Inventor: Nattaporn Lohitharn, Chantilly, VA (US)

(73) Assignee: Logos Technologies, LLC, Chantilly, VA (US)

( * ) Notice: Subject to any disclaimer, the term of this patent is extended or adjusted under 35 U.S.C. 154(b) by 9 days.

(21) Appl. No.: 15/146,508

(22) Filed: May 4, 2016

(65) Prior Publication Data

US 2016/0326561 A1  Nov. 10, 2016

Related U.S. Application Data

(60) Provisional application No. 62/157,101, filed on May 5, 2015.

(51) Int. Cl.
*C12P 19/44* (2006.01)
(52) U.S. Cl.
CPC .................................. *C12P 19/44* (2013.01)
(58) Field of Classification Search
None
See application file for complete search history.

(56) References Cited

U.S. PATENT DOCUMENTS

| 4,628,030 | A |   | 12/1986 | Kaeppeli |
| 5,501,966 | A | * | 3/1996 | Giani et al. |
| 5,658,798 | A |   | 8/1997 | Gunther |
| 7,202,063 | B1 |   | 4/2007 | Gunther |

FOREIGN PATENT DOCUMENTS

| CN | 104312942 A | 1/2015 |
| CN | 104498526 A | 4/2015 |
| KR | 1020130084760 A | 7/2013 |

OTHER PUBLICATIONS

Pornsunthorntawee et al., Bioresource Technology, 2009, vol. 100, p. 812-818.*
Heyd et al., Dissertation, 2009, 154 pages.*
S. George, Thesis, 2010, pp. 122-124 Only.*
Related PCT appln. No. PCT/US2016/03072I, International Search Report and Written Opinion dated Aug. 12, 2016.
Banat et al. (2010) "Microbial biosurfactants production, applications and future potential" Appl. Microbiol. Biotechnol. 87:427-444.
Ghomi et al (2012) "Comparison between batch and fed-batch production of rhamnolipid by Pseudomonas aeruginosa" Iranian J Biotech 10: 263-269.
Gong et al (2015) "Rhamnolipid production, characterization and fermentation scale-up by Pseudomonas aeruginosa with plant oils" Biotechnol Lett 37: 2033-2038.
McNeil and Harvey (2008) "Practical fermentation technology" John Wiley & Sons Ltd, England.
Muller et al. (2012) "Rhamnolipids—Next generation surfactants?", J Biotechnol 162(4):366-80.
Neto et al (2009) "Production of rhamnolipids in solid-state cultivation: characterization downstream processing and application in the cleaning of contaminated soil", Biotechnol J 4: 748-755.
Nitschke et al (2011) "Rhamnolipids and PHAs: Recent reports on Pseudomonas-derived molecules of increasing industrial interest", Proc Biochem 46: 621-630.
Randhawa et al. (2014) "Rhamnolipid biosurfactants—past, present, and future scenario of global market", Frontiers in Microbiology 5:1-7.
Wang et al (2007) "Engineering Bacteria for Production of Rhamnolipid as an Agent for Enhanced Oil Recovery", Biotech. and Bioeng. 98: 842-853.
Wittgens et al. (2011) "Growth independent rhamnolipid production from glucose using the non-pathogenic Pseudomonas putida KT2440" Microbial Cell Factories 10: 80-98.
Zhu et al (2012) Enhanced rhamnolipids production by Pseudomonas aeruginosa based on a pH stage-controlled fed-batch fermentation process, Bioresource Technology 117: 208-213.
Rhaman et al. (2010), "Production of rhamnolipid biosurfactants by Pseudomonas aeruginosa DS10-129 in a microfluidic bioreactor", Biotechnology and Applied Biochemistry 55:45-52.
Mendes et al. (2015), "Physicochemical Properties of Rhamnolipid Biosurfactant from Pseudomonas aeruginosa PA1 to Applications in Microemulsions", J Biomaterials and Nanobiotechnology 6:64-79.

* cited by examiner

*Primary Examiner* — Kade Ariani
(74) *Attorney, Agent, or Firm* — Cheryl Afris; Agris & von Natzmer, LLP (57) ABSTRACT

Provided is a semi-continuous fermentation method of a rhamnolipid producing microorganism to produce rhamnolipids. The fermentation may be run as a batch process but at the end of the fermentation, at least about 70% of the fermentation medium comprising one or more rhamnolipids is drawn out and the new culture medium (feedstock) is fed in as a replacement. This process may be repeated for at least about one month without having to sacrifice RL yield and titer. It allows the fermenter to be utilized at a higher capacity with less downtime for clean-up compared to batch and fed batch fermentation strategies.

40 Claims, 3 Drawing Sheets

SEMI-CONTINUOUS PROCESS FOR THE PRODUCTION OF RHAMNOLIPIDS AT HIGH YIELD AND TITER

TECHNICAL FIELD

Provided is a semi-continuous fermentation method of a rhamnolipid producing microorganism to produce rhamnolipids. The fermentation may be run as a batch process but at the end of the fermentation, at least about 70% of the fermentation medium comprising one or more rhamnolipids is drawn out and the new culture medium (feedstock) is fed in as a replacement.

BACKGROUND

Rhamnolipids (RL), an interface-active glycolipid type biosurfactant, having the properties to lower the surface tension between two different liquids are broadly used as emulsifier, detergents and foaming agents [1-3]. Rhamnolipids are shown to be able to efficiently remove crude oil from contaminated soil and facilitate bioremediation of oil spills due to their emulsification properties which so called "enhanced oil recovery (EOR)" [4]. They have also been used in agriculture due to their antimicrobial and antifungal properties. Rhamnolipids are currently available in an agricultural anti-fungal product marketed as ZONIX and in an industrial cleaning product, RECO, for cleaning oil from storage tanks.

The genus Pseudomonas and E. coli are shown to be capable of producing rhamnolipid (RL) from a variety of carbon and nitrogen sources [5]. Although, the genus Pseudomonas produces higher RL yields and titers than the E. coli [5, 6], the RL concentration is not high enough to make the fermentation process commercially viable. A number of approaches have been carried out to increase the RL productivity including different carbon sources, genetic modified strains and fermentation strategy which appears to be the most effective route to achieve.

Batch and fed batch fermentation are the most common fermentation process with Pseudomonas [7-11]. Batch fermentation is the simplest cultivation method [7,8] in which feedstock (carbon source) is added in the fermenter at the beginning with the inoculum. The fermentation takes place until the feedstock is all utilized by the microorganisms, then the fermenter is shut down and the new batch is started [9]. Fed batch, on the other hand, is batch fermentation but with the addition of feedstock (carbon source), after the feedstock is fully utilized, over the course of fermentation [9-11]. The best up-to-date reported RL titer (productivity) is about 0.58-0.72 g/L/h obtained from fed-batch fermentation of P. aeruginosa [10]. However, this process requires the shutdown of fermenter after 90-120 hours prior to starting up a new fed batch. Similarly, U.S. Pat. No. 5,501,966 reported a 78 g/L of rhamnolipids produced after 167 hours [8] which is too long to operate.

TABLE 1

Summary of various rhamnolipid (RL) fermentation processes by P. aeruginosa

| Fermentation type | RL (g/L) | Fermentation time (h) | RL titer (g/L/h) | Reference |
| --- | --- | --- | --- | --- |
| Batch | 70 | 144 | 0.49 | [7] |
| Batch | 78 | 167 | 0.47 | [8] |

TABLE 1-continued

Summary of various rhamnolipid (RL) fermentation processes by P. aeruginosa

| Fermentation type | RL (g/L) | Fermentation time (h) | RL titer (g/L/h) | Reference |
| --- | --- | --- | --- | --- |
| Fed batch | 65 | 90 | 0.72 | [10] |
| Fed batch | 70 | 120 | 0.58 | [10] |
| Fed batch | 4.1 | 72 | 0.06 | [11] |
| Solid state | 46 | 288 | 0.16 | [12] |

SUMMARY

Provided herein is a semi-continuous fermentation method for producing a plurality of fermentations comprising one or more rhamnolipids comprising (a) Culturing a rhamnolipid producing microorganism in culture medium comprising at least one carbon source, at least one nitrogen source, at least one phosphorous source, at least one magnesium source, at least one potassium source, at least one sulfur source, at least one chloride source, and at least one sodium source between about 2 to about 5 days to obtain a first fermentation medium comprising one or more rhamnolipids;

(b) Removing at least about 70% and more particularly between about 70% to about 80%, or alternatively between about 70 to about 90% of the fermentation medium comprising one or more rhamnolipids obtained in (a);

(c) Replacing said fermentation medium comprising one or more rhamnolipids removed in (b) with culture medium having the composition set forth in step (a);

(d) Repeating steps (a)-(c) at least one time to obtain a subsequent fermentation comprising rhamnolipids
Wherein said steps (a)-(c) are capable of being repeated for at least about 30 days.

In a particular embodiment, said rhamnolipid producing microorganism may be cultured at a temperature of about 25-40 C and more particularly at a temperature of about 30-37 C and/or at a pH of about 5.5 to about 9 and more particularly at a pH of about 6-8.6. The pH at the start of the fermentation after the new culture medium is replaced in step (c) may in a particular embodiment, be around 6-7, preferably 6.2-6.5. The pH of the fermentation does not need to be controlled over the course of fermentation.

In another particular embodiment, said method further comprises adding a composition comprising one or more micronutrients. In a particular embodiment, said micronutrient is present in no more than about 20 mg/L. In a particular embodiment, said micronutrient is present between about 1 mg/L to about 14 mg/L. Said composition may be added either daily or continuously at 0.1% v/v of total fermentation volume per day.

The method set forth above may further comprise adding an anti-foaming agent. Said anti-foaming agent may be carbon or silicon based anti-foaming agent.

The process set forth above allows the fermentation to be run as a batch process but at the end of the fermentation, at least about 70% of the fermentation medium comprising one or more rhamnolipids is drawn out and the new culture medium (feedstock) is fed in as a replacement. This process (step (d)) can be repeated for at least about one month and in another embodiment, up to about 180 days without having to sacrifice RL yield and titer. It allows the fermenter to be utilized at a higher capacity with less downtime for clean-up compared to batch and fed batch fermentation strategies. As noted above, said process step (d) is repeated at least once. In a particular embodiment, said process step (d) is repeated at least 5 times.

In a particular embodiment, said method produces rhamnolipid concentrations of at least about 45 g/L and more particularly about 60-80 g/L with rhamnolipid productivity (titer) as high as about 1.6 g/L/h. In a particular embodiment, where the carbon source is an oil, there is only a residual oil composition of no more than about 0.8% w/v detected in step (b).

DEFINITIONS

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this disclosure are incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

It must be noted that as used herein and in the appended claims, the singular forms "a", "and" and "the" include plural references unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. Thus the terms "comprising", "including," containing", "having" etc. shall be read expansively or open-ended and without limitation. When used herein the term "comprising" can be substituted with the term "containing" or sometimes when used herein with the term "having".

As defined herein, a "rhamnolipid" refers to a glycolipid that has a lipid portion that includes one or more, typically linear, saturated or unsaturated β-hydroxy-carboxylic acid moieties and a saccharide portion of one or more units of rhamnose.

The saccharide portion and the lipid portion are linked via a β-glycosidic bond between the 1-OH group of a rhamnose moiety of the saccharide portion and the 3-OH group of a β-hydroxy-carboxylic acid of the lipid portion. Thus the carboxylic group of one carboxylic acid moiety defines the end of the rhamnolipid. Where more than one rhamnose-moiety is included in a rhamnolipid, each of the rhamnose moieties not linked to the lipid portion is linked to another rhamnose moiety via a 1,4 β-glycosidic bond. In embodiments where two or more β-hydroxy-carboxylic acids are present in a rhamnolipid, the β-hydroxy-carboxylic acid moieties are selected independently from each other. β-hydroxy carboxylic acid moieties of a respective plurality of β-hydroxy carboxylic acid moieties may in some embodiments be identical. In some embodiments they are different from each other.

As defined herein, a "micronutrient composition" is a composition comprising a micronutrient present in an amount no more than about 20 mg/L.

The terms "culture medium", "fermentation medium" are synonymous and are used interchangeably.

DETAILED DESCRIPTION

Provided herein is a semi-continuous fermentation method for producing a plurality of fermentations comprising one or more rhamnolipids. In a particular embodiment, the rhamnolipid may have the structure (I).

Where m=2, 1 or 0, in particular 1 or 0, n=1 or 0, or in particular 1, $R^1$ and $R^2$=independently of one another identical or different organic radical with 2 to 24, preferably 5 to 13, carbon atoms, in particular optionally branched, optionally substituted, in particular hydroxyl-substituted, optionally unsaturated, in particularly optionally mono-, di- or triunsaturated, alkyl radical, preferably one selected from the group consisting of pentenyl, heptenyl, nonenyl, undeceny and tridecenyl and (CH2)o-CH$_3$ where o=1 to 23, preferably 4 to 12.

Both the main chain as well as the branches may furthermore contain heteroatoms as for instance N, O, S, Se or Si or a carbon atom may be replaced by one of these heteroatoms. An aliphatic moiety may be substituted or unsubstituted with one or more functional groups. Substituents may be any functional group, as for example, but not limited to, amino, amido, carbonyl, carboxyl, hydroxyl, nitro, thio and sulfonyl.

Rhamnolipid Producing Microorganism

As noted above, the method comprises culturing a rhamnolipid producing microorganism. A rhamnolipid producing microorganism may be a host cell producing rhamnolipids. A recombinant host cell producing rhamnolipids may be a host cell, such as a bacterial cell that expresses a RhlA gene or ortholog thereof and/or a RhlB gene or ortholog thereof, and/or a RhlC gene or ortholog thereof, and/or RhlR gene or ortholog thereof, and/or RhlI gene or ortholog thereof, and/or RhlG gene or ortholog thereof and others.

Alternatively, a "rhamnolipid-producing microorganism" may be any microorganism, such as bacteria, which has the capacity to synthesize/produce rhamnolipids under suitable conditions which includes but is not limited to bacterium of the phyla Actinobacteria, Fimicutes and Proteobacteria. In a particular embodiment, the rhamnolipid-producing microorganism is a bacterium of the Gammaproteobacteria class. In a further embodiment, the rhamnolipid-producing microorganism is a bacterium of the Pseudomonadales order. In yet another further embodiment, the rhamnolipid producing microorganism is a bacterium of the Pseudomonadacae family. In an even further embodiment, the rhamnolipid-producing microorganism is a bacterium of the *Pseudomonas* genus, such as *P. alcaligenes, P. aeruginosa, P. chloro-raphis, P. clemancea, P. collierea, P. fluorescens, P. luteola, P. putida, P. stutzeri* and *P. teessidea*. In a further embodiment, the rhamnolipid-producing microorganism is *P. aeruginosa*.

Culture Medium

The rhamnolipid containing microorganism is cultured in culture medium. Said culture medium comprises at least one carbon source, at least one nitrogen source, at least one phosphorous source, at least one sulfur source, at least one sodium source, at least one magnesium source, at least one potassium source, at least one sulfur source and at least one chloride source.

The carbon source may be a monosaccharide, e.g. glucose, a disaccharide, e.g. sucrose, a sugar alcohol, e.g. glycerol, a long chain alkane, e.g., n-hexadecane, a fatty acid such as caprylic acid (also termed octanoic acid), vegetable oils (fresh or waste; e.g., soybean oil) or mixtures thereof, organic acids (e.g. lactic acid, acetic acid, citric acid, propionic acid), alcohols (e.g. ethanol), and mixtures of these. In a particular embodiment, the carbon source is a vegetable oil selected from the group consisting of olive oil, rapeseed oil, olive oil, corn oil, sunflower oil, canola oil and soybean oil. The carbon source may be present in the amount of about 6% to about 12% w/w.

The nitrogen source may be ammonium sulfate, ammonium phosphate, urea, yeast extract, meat extract, peptone, and corn steep liquor. In a particular embodiment, the nitrogen source is NaNO$_3$. In yet another embodiment, the nitrogen may be present in the amount of about 1-10 g/L.

The phosphorous source may in a particular embodiment be H$_3$PO$_4$ or K$_2$HPO$_4$. In yet another particular embodiment, said phosphorous is present in the amount of about 1-10 g/L.

The magnesium ion in a particular embodiment may be MgSO$_4$*7H2O and/or MgCl$_2$. In a particular embodiment, the magnesium is present in the amount of about 0.01-1 g/L.

The potassium may be KCl and/or KOH. In a particular embodiment, the potassium is present in the amount of about 0.1 to about 2 g/L.

The sodium may be NaCl, NaNO$_3$, and NaOH. In a particular embodiment, said sodium ion is present in the amount of about 1-15 g/L.

The chloride may be KCl and NaCl. In a particular embodiment, said chloride ion is present in the amount of about 0.1-1 g/L.

The sulfur may be H$_2$SO$_4$. In a particular embodiment, said sulfur ion is present in the amount of about 0.1-1 g/L.

The sulfur, chloride and nitrogen sources may be derived from the aqueous layer, or also referred to as the aqueous liquid phase or aqueous phase of an acid treated and aged microorganism containing fermentation medium obtainable using procedures described in application Ser. No. 14/992, 995. In a specific embodiment, the fermentation or culture medium comprising one or more rhamnolipids may be aged by incubating for at least about 1 day and between about 24-72 hrs at between about 0-30 C. In a particular embodiment, the aged aqueous medium may be treated with acid so the culture medium is adjusted to a pH of about 1.5 to 2.5, preferentially, about 2.05 to about 2.15. The acid can be an organic acid such as acetic acid, or a mineral acid. In a preferred embodiment, the acid is a mineral acid, e.g. HCl, H$_2$SO$_4$, HNO$_3$, or H$_3$ClO$_4$. As a result, an aqueous liquid phase, oily phase and solid phase is generated. The aqueous liquid phase is removed using procedures known in the art and in a specific embodiment using methods set forth above (e.g., filtration, or centrifugation or settling combined with decanting).

The culture medium may further comprise an emulsifier. In a particular embodiment, the emulsifier is selected from the group consisting of Arabic gum, guar gum and rhamnolipids. In yet another particular embodiment, the ratio of emulsifier to carbon source in said culture medium is between about 0.1% to about 20% w/w. In yet another particular embodiment, wherein said emulsifier may be present in the amount of about 5-10% by weight.

In a particular embodiment, the culture or fermentation medium is sterilized using methods known in the art. These methods may be filtration based, heat based, chemical based or ultraviolet light radiation based. In a particular embodiment, the heat based treatment may be via moist heat sterilization, particularly autoclaving.

In one embodiment, the aqueous medium (e.g., fermentation medium) may be sterilized by one of the above procedures. In another embodiment, the fermentation media may be sterilized by more than one of the procedures set forth above and these sterilizations could be in any order. It may be sterilized in the fermentation during the first cycle of fermentation, but should be sterilized in another vessel in subsequent cycles.

Micronutrient Composition

As noted above, said method may further comprise adding a micronutrient solution or composition. Said micronutrient may be a trace of Fe, Mn, Zn, Cu, Na. In a particular embodiment, said micronutrient is a Fe, Mn, Zn, Na or Cu salt. In a more particular embodiment said micronutrient composition comprises Fe, Mn, Zn, Na and Cu salts. The composition may be sterilized by filtration.

In particular embodiments, said Cu salt is at least one of CuCl$_2$*2H$_2$O and CuSO$_4$*5H$_2$O and may be present in the amount of about 0.5-3 g/L of micronutrient solution; said Mn salt is at least one of MnSO4*H$_2$O and MnCl$_2$.4H$_2$O and may be present in the amount of about 0.1-1.5 g/L of micronutrient solution; said Zn salt is ZnSO$_4$*7H$_2$O or ZnCl$_2$ and may be present in the amount of about 0.5-3 g/L of micronutrient solution; said Fe salt is at least one of FeCl$_3$*6H$_2$O or FeSO$_4$ and may be present in the amount of about 0.1-1 g/L of micronutrient solution; said sodium salt is Na$_3$C$_6$H$_5$O$_7$*2H$_2$O and may be present in the amount of about 1-5 g/L of micronutrient solution.

DESCRIPTION OF SPECIFIC EMBODIMENTS

EXAMPLE 1

Culture Medium Preparation

A composition of the 8% soybean oil in the culture medium for the fermentation of *Pseudomonas aeruginosa* for rhamnolipids production is shown in Table 2, infra. Gum Arabic is used at 10% w/w of soybean oil.

TABLE 2

Culture Medium Composition

| Component | Concentration |
|---|---|
| Gum Arabic | 8.00 g/L |
| Soybean oil | 80.00 g/L |
| 85% H$_3$PO$_4$ | 9.69 g/L |
| 99% NaOH | 5.21 g/L |
| 99% MgSO$_4$*7H$_2$O | 0.50 g/L |
| 99% KCl | 1.00 g/L |
| 99% NaNO$_3$ | 15.00 g/L |
| 98% H$_2$SO$_4$ | 0.92 g/L |
| Deionized water | The rest |

To make the culture medium, gum Arabic is first dissolved in deionized water to obtain 5% w/w gum Arabic solution under agitation at 150-250 rpm and at 40-45 C in a separate container. This step will take at least 30 min to allow all gum Arabic to dissolve in water. Second, mix soybean oil and 5% gum Arabic solution with deionized water using a blender such as kitchen blender. Make sure it is well mixed to obtain an emulsion (i.e. the solution becomes white like milk). After the emulsion of soybean oil is obtained, H$_3$PO$_4$ is added into the emulsion under stirring and the next chemical NaOH is added in after H$_3$PO$_4$ is well dissolved. The next chemical which are MgSO$_4$ then KCl then NaNO$_3$ and the last H$_2$SO$_4$ are added into the emulsion under stirring. Before adding the next chemical, make sure that it is well dissolved in the emulsion. The culture medium then can be stream sterilized (autoclave).

EXAMPLE 2

Micronutrient Composition Preparation

The composition of micronutrient is shown in Table 3. Please note that the concentration of each salt is in g/L of micronutrient solution.

TABLE 3

Composition of Micronutrient

| Component | Concentration |
|---|---|
| Na$_3$C$_6$H$_5$O$_7$*2H$_2$O | 2.0 g/L |
| FeCl$_3$*6H$_2$O | 0.3 g/L |
| ZnSO$_4$*7H$_2$O | 1.4 g/L |
| CuCl$_2$*2H$_2$O | 1.2 g/L |
| CuSO$_4$*5H$_2$O | 1.2 g/L |
| MnSO$_4$*H$_2$O | 0.8 g/L |

All chemicals are ACS grades (highest purity available). Na$_3$C$_6$H$_5$O$_7$*2H$_2$O is first added into deionized water using stirring. After it is all dissolved, the next chemical which is FeCl$_3$*6H$_2$O can be added in. This step is repeated until all the chemicals listed in the table are added into the solution in the order of FeCl$_3$*6H$_2$O then ZnSO$_4$*7H$_2$O then CuCl$_2$*2H$_2$O then CuSO$_4$*5H$_2$O and MnSO$_4$*H$_2$O the last. The micronutrient can be sterilized using a 0.2 micron sterilized filtration. Do not steam autoclave the micronutrient.

EXAMPLE 3

Seed Culture of *P. aeruginosa* (Schroeter) Migula (R4 Strain)

R4 strain obtained from ATCC #55734 is first inoculated in agar plates containing 40 g/L Tryptic Soy Agar at 32 C for 18-24 hours. After R4 colonies are formed, a single colony is then cultured in 5 ml of 20 g/L LB Broth (Lennox) in a shake tube at 37 C for 20-24 hours. The final OD$_{600}$ is about 3-5 and the LB Broth (Lennox) solution in the shake tube will change from yellow to green. Then, the R4 culture obtained from a shake tube is inoculated in a shake flask containing 20 g/L LB Broth (Lennox) at 1% inoculation and incubated at 37 C for 20-24 hours. This process is repeated as necessary in order to generate sufficient inoculum of R4 required for the fermentation. The LB Broth (Lennox) is obtained from Sigma Aldrich #3022 which contains 10 g/L Tryptone, 5 g/L yeast extract and 5 g/L NaCl.

EXAMPLE 4

Figure 1:
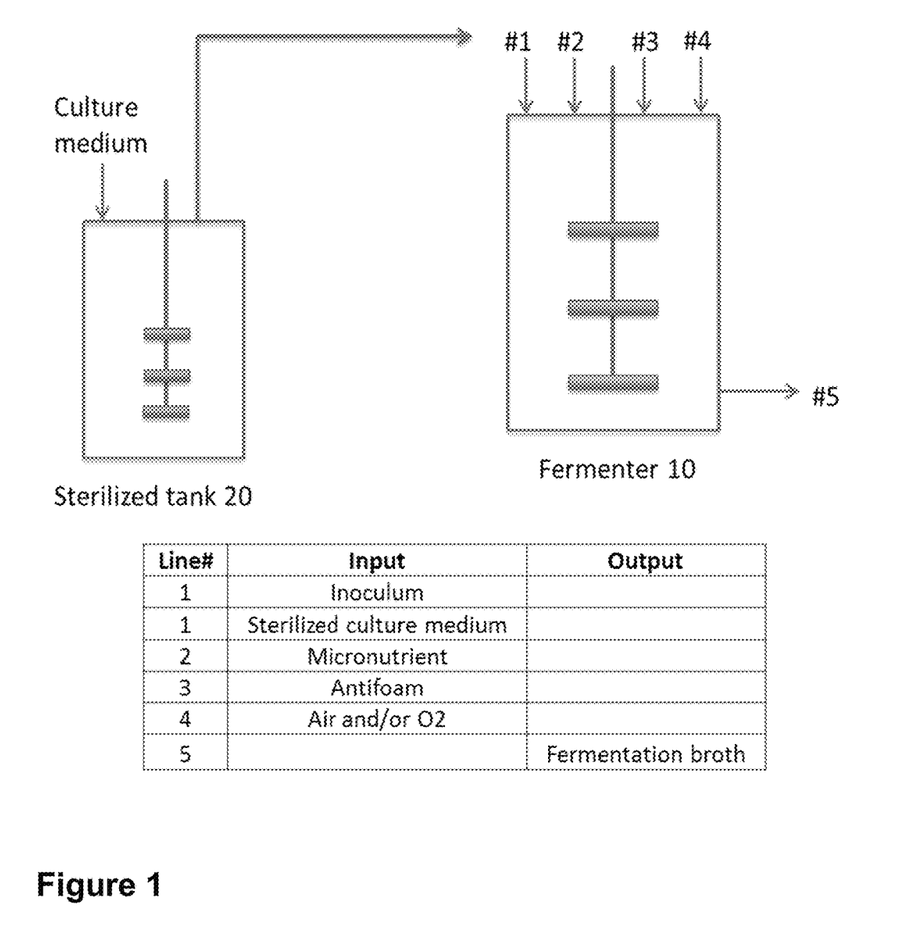
FIG. 1 is a schematic depiction of the semi-continuous fermentation method for producing rhamnolipids.

Semi-Continuous Fermentation of Rhamnolipids with Deionized Water and 10% w/w Gum Arabic (as Emulsifier) to Soybean Oil The fermentation of *P. aeruginosa* (Schroeter) Migula obtained from ATCC #55734 (R4) is performed in 10 L bioreactor and is schematically set forth in FIG. 1. It is initiated with the preparation of 8 of the culture medium of 8% soybean oil and 10% w/w gum Arabic to soybean oil in the fermenter 10. The chemicals used in the culture medium in Example 1 are ACS grades (highest purity available). After sterilization of the culture medium, the temperature is cooled down to 37 C using a water heating jacket and the agitation starts (250 rpm). Once the temperature is stable at 37 C, 0.2 micron filtered air is supplied to the fermenter thru aeration line (#4) at 1.5 L/min and the fermenter is inoculated with 2.5% (200 ml) inoculum of R4 obtained from Example 3 thru line #1. Filter sterilized 8 ml micronutrient prepared in Example 2 is then added to the fermenter thru line #2 once a day. In the case when the micronutrient cannot be added daily, 8 ml micronutrient is diluted in 32 ml of deionized water (per day) in order to be added continuously in the fermenter at 40 ml/day using a peristatic pump.

Silicon based antifoam (Sigma Aldrich #85390) is automatically added to knock down the foam during fermentation thru line #3.

The fermentation is run at a temperature of 37 C with the initial pH of the culture medium of 6.2 with no pH control over the course of fermentation. The stirring rate automatically increases as necessary in order to keep % dissolved oxygen (% DO) at 15%-20%. The stirring rate goes up 500 rpm before the air flow rate increases from 1.5 to 3.5 L/min at 40-48 hours post inoculation in order to keep up with the oxygen demand of the microbes during growth rate. After 60 hours post inoculation, the pH is increasing after it slightly dips down (or remains stable). Additionally, the % DO increases while the agitation and air flow are at the lowest values (250 rpm and 1.5 L/min, respectively) indicating that the fermentation is completed at 72 hours. This can be confirmed with a residual soybean oil in fermentation medium comprising one or more rhamnolipids to be less than 0.8%.

Figure 2:
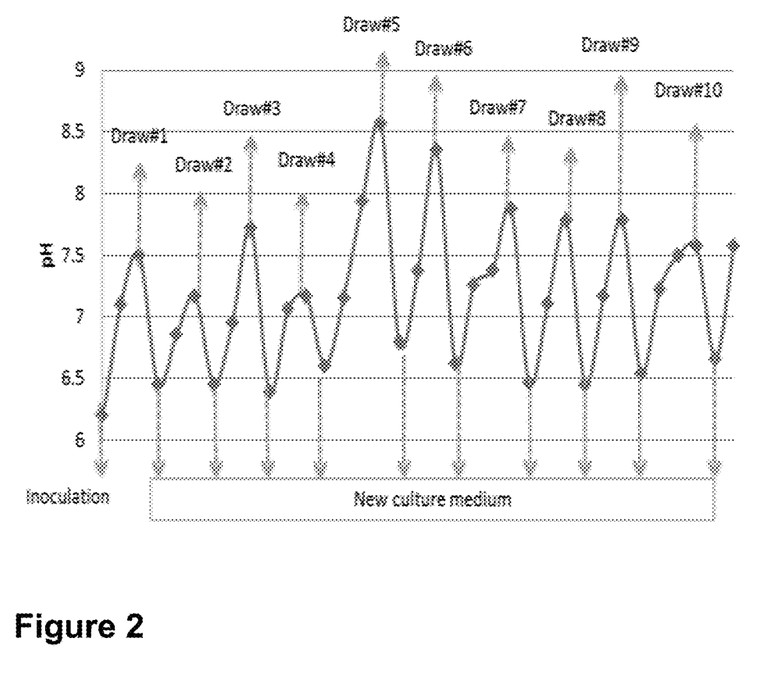
FIG. 2 shows the change in pH over the course of fermentation with steps (a)-(c) being repeated for more than 30 days in Example 4.

The peristatic pump is then started to remove 6 L (75% of the total) of the fermentation medium comprising one or more rhamnolipids thru line #5. Once 6 L of broth is removed which so called "Draw#1", the recently sterilized 6 L of 8% soybean oil culture medium prepared in sterilized tank 20 is fed into the fermenter 10 using a gravity feed. The initial fermentation pH is 6.5. The fermentation parameters described in the above paragraph are used. In this case, after 48 hours, the fermentation is completed and 75% of the fermentation medium comprising one or more rhamnolipids is being ready to be drawn out (Draw#2). Subsequently, the next batch of sterilized soybean oil culture medium is fed in from the sterilized tank 20. The process repeats for 6 weeks with no sign of loss in rhamnolipids yields and titers before the fermenter is shut down for cleaning. A change in pH over the course of fermentation between the drawing and for each drawing is shown in the FIG. 2. The rhamnolipid (RL) concentration and titer are shown in Table 4 infra. The rhamnolipid (RL) concentration of all of the 12 draws is at least 62 g/L up to 79 g/L. The RL productivity (titer) is 0.92-1.61 g/L/h.

TABLE 4

Rhamnolipid Conc and Titer During Semi-Continuous Fermentation With Soybean Oil

| Draw# | % Initial Soybean oil | Fermentation time (between draw) (h) | Total RL (g/L) | RL titer (g/L/h) | Micronutrient |
|---|---|---|---|---|---|
| 1 | 8.0% | 72 | 66 | 0.92 | Continuously added |
| 2 | 6.0% | 48 | 62 | 1.29 | |
| 3 | 6.0% | 46 | 71 | 1.54 | |
| 4 | 7.5% | 69 | 77 | 1.12 | |
| 5 | 6.0% | 46 | 74 | 1.61 | Added daily |
| 6 | 6.0% | 48 | 74 | 1.54 | |
| 7 | 7.5% | 71 | 79 | 1.11 | |
| 8 | 6.0% | 47 | 70 | 1.49 | |
| 9 | 6.0% | 46 | 66 | 1.43 | |
| 10 | 7.5% | 69 | 65 | 0.94 | Continuously added |
| 11 | 6.0% | 48 | 68 | 1.42 | |
| 12 | 6.0% | 48 | 69 | 1.44 | |

EXAMPLE 5

Semi-Continuous Fermentation of Rhamnolipids with Deionized Water, 5% w/w Gum Arabic to Soybean Oil with Continuously Added Micronutrient The composition of the culture medium used in Table 5. 7.3 L of 8% soybean oil with 5% w/w gum Arabic to soybean oil is prepared as described in Example 1. All chemicals used in this example are industry grade containing impurities.

TABLE 5

Composition of Culture Medium w/5% Gum Arabic, 8% Soybean Oil and 5% R4 Inoculum

| Component | Concentration |
|---|---|
| Gum Arabic | 4.00 g/L |
| Soybean oil | 80.00 g/L |
| 85% $H_3PO_4$ | 9.69 g/L |
| 99% NaOH | 5.21 g/L |
| 99% $MgSO_4 \cdot 7H_2O$ | 0.50 g/L |
| 99% KCl | 1.00 g/L |
| 99% $NaNO_3$ | 15.00 g/L |
| 98% $H_2SO_4$ | 0.92 g/L |
| Deionized water | The rest |

Figure 3:
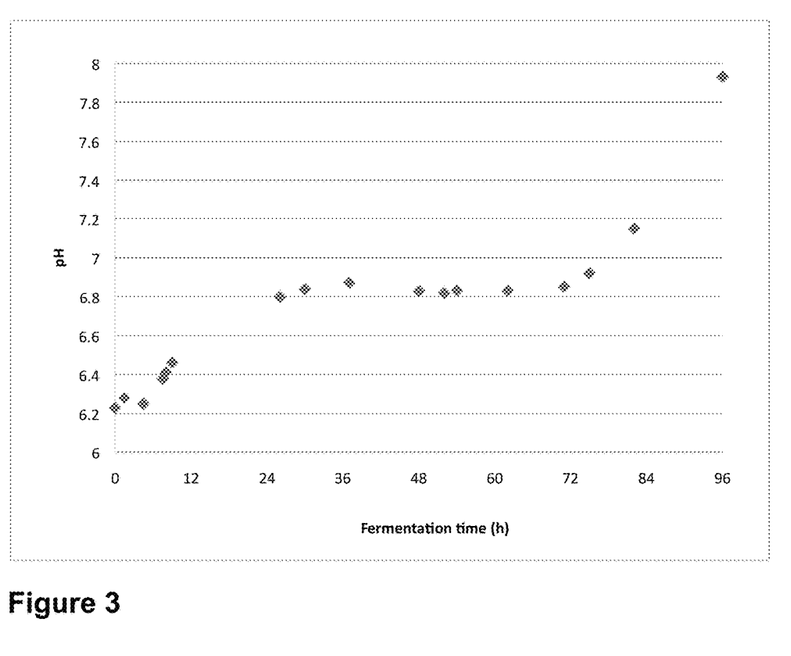
FIG. 3 shows the change in pH over the course of fermentation after post inoculation or after filling with the new culture medium in Example 5.

The fermentation is run as in Example 4 except that 5% (360 ml) R4 inoculum is used to inoculate the fermenter and 77% of the fermentation medium comprising one or more rhamnolipids (5.6 L) is drawn out and the new culture medium contains 5% w/w gum Arabic to soybean oil. Micronutrient is prepared as described in Example 2. By diluting 7.3 ml of micronutrient in 32.7 ml deionized water (per day), it is added continuously at the flow rate of 40 ml/day using a peristatic pump. Silicon based antifoam (DOW AFE-1510) is automatically added to knock down the foam during fermentation. The stirring rate automatically increases as necessary in order to keep % dissolved oxygen (% DO) at 15%-20% with air flow rate of 1.5 L/min. Pure oxygen is additionally added to the fermenter at 0.005-0.1 L/min in order to keep the agitation down and thus, less foaming issue. A typical change in pH over the course of fermentation post inoculation or after filling with the new culture medium is shown in FIG. 3. The rhamnolipid (RL) concentration and titer are shown in Table 6 infra.

TABLE 6

Rhamnolipid Conc and Titer Using Semi-Continuous Method Using 5% R4 Inoculum

| Draw# | % Initial Soybean oil | Fermentation time (between draw) (h) | Total RL (g/L) | RL titer (g/L/h) |
|---|---|---|---|---|
| 1 | 8.0% | 59 | 56 | 0.90 |
| 2 | 7.7% | 70 | 79 | 1.13 |
| 3 | 6.1% | 65 | 76 | 1.17 |
| 4 | 8.0% | 96 | 70 | 0.73 |
| 5 | 7.7% | 91 | 76 | 0.84 |
| 6 | 8.0% | 82 | 70 | 0.85 |
| 7 | 7.7% | 70 | 78 | 1.11 |

EXAMPLE 6

Semi-Continuous Fermentation of Rhamnolipids with Deionized Water, 5% w/w Gum Arabic to Soybean Oil with Continuously Added 2× of Micronutrient In this example, the culture medium and fermentation parameters are the same as shown in Example 5 except that the amount of micronutrient used is double. By diluting 14.6 ml of micronutrient (prepared in Example 2) in 26.4 ml deionized water (per day), it is added continuously at the flow rate of 40 ml/day using a peristatic pump. The stirring rate automatically increases as necessary in order to keep % dissolved oxygen (% DO) at 15%-20% with air flow rate of 1.5 L/min. Pure oxygen is additionally added to the fermenter at 10-30% of air flow to keep the total flow rate constant at 1.5 L/min in order to keep the agitation down and thus, less foaming issue. The rhamnolipid (RL) concentration and titer are shown in Table 7 infra.

TABLE 7

RL Conc and Titer During Semi-Continuous Fermentation With 2X Micronutrient

| Draw# | % Initial Soybean oil | Fermentation time (between draw) (h) | Total RL (g/L) | RL titer (g/L/h) |
|---|---|---|---|---|
| 1 | 7.7% | 73 | 75 | 1.03 |
| 2 | 6.1% | 48 | 64 | 1.33 |
| 3 | 7.7% | 68 | 69 | 1.01 |
| 4 | 6.1% | 69 | 66 | 0.96 |

EXAMPLE 7

Semi-Continuous Fermentation of Rhamnolipids with 8% Soybean Oil and 85% Cold Tap Water/15% Aqueous Top Layer Waste Stream from Fermentation Medium Comprising One or More Rhamnolipids The composition of the culture medium used in this Example is shown in Table 8.

TABLE 8

Culture Medium with Aqueous Layer

| Component | Concentration |
|---|---|
| Soybean oil | 80.00 g/L |
| 85% $H_3PO_4$ | 9.69 g/L |
| 99% NaOH | 5.21 g/L |
| 99% $MgSO_4 \cdot 7H_2O$ | 0.50 g/L |
| 99% KCl | 1.00 g/L |
| 99% $NaNO_3$ | 15.00 g/L |
| Aqueous layer waste water | 150.00 g/L |
| Cold tap water | The rest |

The aqueous top layer waste stream may be obtained using the procedures described in U.S. application Ser. No. 14/992,995, filed Jan. 11, 2016 (See Example 3 of said application). Briefly, aqueous top layer waste stream is obtained from clarified fermentation broth. Clarified broth is made by allowing fermentation medium containing P. aeroginosa that ends at a pH of 6.0 to 6.5 to age under ambient conditions for about 2 days. The biomass settles to the bottom of the vessel used for this aging process and the clear supernatant, after removal, is clarified broth. The next step in the process is to add acid, such as concentrated sulfuric acid, until the pH is about 2.1. The rhamnolipids precipitate out of solution and form a solid phase and an oily liquid phase at the bottom of the vessel used for this step. The separation of the solid and oily liquid phases can be sped up by centrifugation. The solid and oily liquid phases are separated from the aqueous top phase or layer, which can be discarded or recycled. The above-referenced aqueous layer is a source of $H_2SO_4$ and micronutrients of which 15% w/w is used in the culture medium with 8% soybean oil in the balance of cold tap water. The waste stream aqueous top layer is first filtered at 1 micron to remove large particles prior to its use.

7.3 L of the culture medium containing 8% soybean oil with 15% waste stream aqueous top layer and cold tap water is prepared by first mixing soybean oil, aqueous top layer and cold tap water using a kitchen blender. After they all are well mixed, $H_3PO_4$, NaOH, $MgSO_4$, KCl and $NaNO_3$ are added into the solution in that order under stirring. The culture medium then can be stream sterilized (autoclave). All chemicals used in this example are industry grade containing impurities.

The fermentation is carried out at the same parameters as Example 5. Micronutrient composition is added continuously. Pure oxygen is additionally added to the fermenter at 10-30% of air flow to keep the total flow rate constant at 1.5 L/min in order to keep the agitation down and thus, less foaming issue. The rhamnolipid (RL) concentration and titer are shown in Table 9 infra.

TABLE 9

RL Conc and Titer During Semi-Continuous Fermentation (Aqueous Layer)

| Draw# | % Initial Soybean oil | Fermentation time (between draw) (h) | Total RL (g/L) | RL titer (g/L/h) |
|---|---|---|---|---|
| 1 | 8.0% | 95 | 74 | 0.78 |
| 2 | 6.1% | 75 | 64 | 0.85 |
| 3 | 7.7% | 92 | 73 | 0.79 |
| 4 | 6.1% | 60 | 62 | 1.03 |
| 5 | 7.7% | 83 | 71 | 0.85 |
| 6 | 6.1% | 71 | 68 | 0.96 |
| 7 | 7.7% | 89 | 77 | 0.86 |

EXAMPLE 8

Semi-Continuous Fermentation of Rhamnolipids in 100 L Scale

100 L of the culture medium (composition as in Example 5) is prepared as in Example 1 and sterilized in 120 L bioreactor. Its composition is shown in Table 10. Seed culture of R4 strain is prepared according to Example 2. The 100 L fermenter is inoculated with 2.9 L R4 strain incubated in a shake flask at 37 C for 24 hours in 20 g/L LB Broth Lennox.

The fermentation is run at a temperature of 37 C with the initial pH of the culture medium of 6.2 with no pH control over the course of fermentation. Silicon based antifoam (DOW AFE-1510) is diluted with 50% deionized water which is then autoclaved prior to use. The antifoam is automatically added to knock down the foam during fermentation. The agitation is at 150 rpm with 17 L/min of air. The stirring rate automatically increases as necessary in order to keep % dissolved oxygen (% DO) at 15%-20%. 800 ml of micronutrient prepared and composition as Example 2 is diluted with 2.2 L deionized water and thus, it is being fed in continuously at 375 ml/day for 8 days.

70 L of culture medium containing 9% soybean oil (composition in Table 10 infra) is prepared as in Example 1 and is sterilized in a different 100 L bioreactor a day prior to the draw. After 105 hours post inoculation, the pH starts to increase after it remains constant around 7. The fermentation is completed at 115 hours with a pH at 7.3.

TABLE 10

Composition of 9% Soybean Oil Culture Medium (70 L)

| Component | Concentration |
|---|---|
| Gum Arabic | 4.50 g/L |
| Soybean oil | 90.00 g/L |
| 85% $H_3PO_4$ | 9.69 g/L |
| 99% NaOH | 5.21 g/L |
| 99% $MgSO_4 \cdot 7H_2O$ | 0.50 g/L |
| 99% KCl | 1.00 g/L |
| 99% $NaNO_3$ | 15.00 g/L |
| 98% $H_2SO_4$ | 0.92 g/L |
| Deionized water | The rest |

After 115 hours post inoculation, the peristatic pump is then started to remove 70 L (70% of the total) of the fermentation medium comprising one or more rhamnolipids. Once 70 L of broth is removed which so called "Draw#1", the recently sterilized 70 L of 9% soybean oil culture medium is fed into the fermenter using a peristatic pump. The initial fermentation pH is 6.5. The fermentation parameters described in the above paragraph are used. In this case, after 70 hours, the fermentation is completed with a pH at 7.14. The rhamnolipid (RL) concentration and titer are shown in Table 11 infra.

TABLE 11

RL Concentration and Tier (100 L Scale)

| Draw# | % Initial Soybean oil | Fermentation time (between draw) (h) | Total RL (g/L) | RL titer (g/L/h) |
|---|---|---|---|---|
| 1 | 8% | 115 | 70 | 0.61 |
| 2 | 6.3% | 70 | 75 | 1.07 |

EXAMPLE 9

Shake Flask Experiment without Micronutrient 50 ml of culture medium (composition as below) is prepared as Example 1 in a 250 ml shake flask. Its composition is shown in Table 12. After being autoclaved and cooled down to room temperature, the shake flasks are inoculated with 5% frozen stock of R4 strain. The frozen stock is obtained from mixing 70% R4 tube culture having $OD_{600}$ of 3-4 with 30% glycerol and stored at −80 C. The incubation is carried out at 37 C in a shaker for 92 hours without the addition of micronutrient. After 92 hours post inoculation, the rhamnolipid concentrations are average 47±3 g/L for 5 shake flasks.

TABLE 12

Culture Medium Concentration For Use In Fermentation Without Micronutrient

| Component | Concentration |
|---|---|
| Gum Arabic | 6.00 g/L |
| Soybean oil | 60.00 g/L |
| 85% $H_3PO_4$ | 9.69 g/L |
| 99% NaOH | 5.21 g/L |
| 99% $MgSO_4 \cdot 7H_2O$ | 0.50 g/L |
| 99% KCl | 1.00 g/L |
| 99% $NaNO_3$ | 15.00 g/L |
| 98% $H_2SO_4$ | 0.92 g/L |
| Deionized water | The rest |

REFERENCES

[1] Randhawa et al. (2014) "Rhamnolipid biosurfactants—past, present, and future scenario of global market", Frontiers in Microbiology 5:1-7.
[2] Muller et al. (2012) "Rhamnolipids—Next generation surfactants?", J Biotechnol 162(4):366-80.
[3] Banat et al. (2010) "Microbial biosurfactants production, applications and future potential" Appl. Microbiol. Biotechnol. 87:427-444.
[4] Wang et al (2007) "Engineering Bacteria for Production of Rhamnolipid as an Agent for Enhanced Oil Recovery" Biotech. and Bioeng. 98: 842-853.
[5] Wittgens et al. (2011) "Growth independent rhamnolipid production from glucose using the non-pathogenic *Pseudomonas putida* KT2440" Microbial Cell Factories 10: 80-98.
[6] Nitschke et al (2011) "Rhamnolipids and PHAs: Recent reports on *Pseudomonas*-derived molecules of increasing industrial interest" Proc Biochem 46: 621-630.
[7] Gong et al (2015) "Rhamnolipid production, characterization and fermentation scale-up by *Pseudomonas aeruginosa* with plant oils" Biotechnol Lett 37: 2033-2038.
[8] Giani et al (1997) "*Pseudomonas Aeruginosa* and its use in a process for the biotechnological preparation of L-rhamnose" U.S. Pat. No. 5,501,966.
[9] Mcneil and Harvey (2008) "Practical fermentation technology" John Wiley & Sons Ltd, England.
[10] Zhu et al (2012) "Enhanced rhamnolipids production by *Pseudomonas aeruginosa* based on a pH stage-controlled fed-batch fermentation process, Bioresource Technology 117: 208-213.
[11] Ghomi et al (2012) "Comparison between batch and fed-batch production of rhamnolipid by *Pseudomonas aeruginosa*" Iranian J Biotech 10: 263-269.
[12] Camilios et al (2009) "Production of rhamnolipids in solid-state cultivation: characterization downstream processing and application in the cleaning of contaminated soil" Biotechnol J 4: 748-755.

What is claimed is:

1. A semi-continuous method for producing a plurality of fermentation media comprising one or more rhamnolipids comprising:
(a) culturing a rhamnolipid producing *Pseudomonas aeruginosa* in culture medium comprising at least one vegetable oil as a carbon source, an emulsifier, at least one nitrogen source, at least one phosphorous source, at least one magnesium source, at least one potassium source, at least one sulfur source, at least one chloride source, and at least one sodium source between for about 2 to about 5 days to obtain a first fermentation medium comprising one or more rhamnolipids;
  (b) removing at least about 70% of the total volume of said first fermentation medium obtained in (a), wherein said first fermentation medium removed comprises one or more rhamnolipids;
  (c) replacing said first fermentation medium removed in (b) with culture medium having the composition set forth in step (a);
  (d) repeating steps (a)-(c) at least one time to obtain a subsequent fermentation medium comprising rhamnolipids wherein at least about 45 g/L of rhamnolipids are produced.

2. The method according to claim 1, wherein said emulsifier is selected from the group consisting of Arabic gum, guar gum and rhamnolipids.

3. The method according to claim 1, wherein said emulsifier is present in the amount of about 0.1-20% by weight.

4. The method according to claim 1, wherein said vegetable oil is selected from the group consisting of olive oil, rapeseed oil, corn oil, sunflower oil, canola oil and soybean oil.

5. The method according to claim 1, wherein said carbon source is present at a concentration of about 6-12% by weight.

6. The method according to claim 1, wherein said nitrogen source is selected from the group consisting of $NaNO_3$, Urea ($CO(NH_2)_2$) and $NH_4Cl$.

7. The method according to claim 1, wherein said nitrogen source is present in the amount of about 1-4 g/L.

8. The method according to claim 1, wherein said phosphorous source is selected from the group consisting of $H_3PO_4$ and $K_2HPO_4$.

9. The method according to claim 1, wherein said phosphorous source is present in the amount of about 1-3 g/L.

10. The method according to claim 1, wherein said magnesium source is selected form the group consisting of $MgSO_4.7H_2O$ and $MgCl_2$.

11. The method according to claim 1, wherein said magnesium source is present in the amount of about 0.001-0.2 g/L.

12. The method according to claim 1, wherein said potassium source is KCl and KOH.

13. The method according to claim 1, wherein said potassium source is present in the amount of about 0.1 to about 1 g/L.

14. The method according to claim 1, wherein said sodium source is NaCl, $NaNO_3$, and NaOH.

15. The method according to claim 1, wherein said sodium source is present in the amount of about 1-10 g/L.

16. The method according to claim 1, wherein said chloride source is KCl and NaCl.

17. The method according to claim 1, wherein said chloride source is present in the amount of about 0.1-1 g/L.

18. The method according to claim 1, wherein said sulfur source is $H_2SO_4$.

19. The method according to claim 1, wherein said sulfur source is present in the amount of about 0.1-1 g/L.

20. The method according to claim 1, which further comprises adding a composition comprising one or more micronutrients at a concentration of no more than 20 mg/L of micronutrient solution to said culture medium in step (a) at 0.1% v/v of total fermentation volume per day.

21. The method according to claim 20, wherein said micronutrient is a Fe, Mn, Zn, Na or Cu salt.

22. The method according to claim 21, wherein said Cu salt is at least one of $CuCl_2.2H_2O$ and $CuSO_4.5H_2O$.

23. The method according to claim 21, wherein said Cu salt is present in the amount of about 0.5-3 g/L of micronutrient solution.

24. The method according to claim 21, wherein said Mn is at least one of $MnSO4.H_2O$ and $MnCl_2.4H_2O$.

25. The method according to claim 21, wherein said Mn is present in the amount of about 0.1-1.5 g/L of micronutrient solution.

26. The method according to claim 21, wherein said Zn is $ZnSO_4.7H_2O$ or $ZnCl_2$.

27. The method according to claim 21, wherein said Zn is present in the amount of about 0.5.

28. The method according to claim 21, wherein said Fe is at least one of $FeCl_3.6H_2O$ or $FeSO_4$.

29. The method according to claim 21, wherein said Fe is present in the amount of about 0.1-1 g/L of micronutrient solution.

30. The method according to claim 21, wherein said sodium salt is $Na_3C_6H_5O_7.2H_2O$, $NaC_6H_7O_7$, and $Na_2C_6H_6O_7$.

31. The method according to claim 21, wherein said sodium salt is present in the amount of about 1-5 g/L of micronutrient solution.

32. The method according to claim 20, wherein said micronutrient composition is added continuously.

33. The method according to claim 20, wherein said micronutrient composition is added daily.

34. The method according to claim 1, wherein said method further comprises adding anti-foam.

35. The method according to claim 34, wherein said anti-foam is silicon-based or carbon-based anti-foam.

36. The method according to claim 1, wherein said *Pseudomonas aeruginosa* is cultured at a temperature of about 30-37 ° C. and/or at a pH of about 6-8.6.

37. The method according to claim 1, wherein step (d) is repeated for at least about 30 days.

38. The method according to claim 1, wherein said carbon source is vegetable oil.

39. The method according to claim 20, wherein said composition comprises a Fe, Mn, Zn, Na and Cu salt.

40. The method according to claim 1, wherein said method further comprises adding an emulsifier to said culture medium prior to beginning said culturing step (a).

* * * * *